United States Patent
Sen et al.

(10) Patent No.: US 10,628,738 B2
(45) Date of Patent: Apr. 21, 2020

(54) STANCE CLASSIFICATION OF MULTI-PERSPECTIVE CONSUMER HEALTH INFORMATION

(71) Applicant: Conduent Business Services, LLC, Dallas, TX (US)

(72) Inventors: Anirban Sen, West Bengal (IN); Sandya Mannarswamy, Karnataka (IN); Manjira Sinha, West Bengal (IN); Shourya Roy, Karnataka (IN)

(73) Assignee: Conduent Business Services, LLC, Florham Park, NJ (US)

( * ) Notice: Subject to any disclaimer, the term of this patent is extended or adjusted under 35 U.S.C. 154(b) by 535 days.

(21) Appl. No.: 15/420,355

(22) Filed: Jan. 31, 2017

(65) Prior Publication Data

US 2018/0218253 A1    Aug. 2, 2018

(51) Int. Cl.
| | | |
|---|---|---|
| *G06N 3/08* | (2006.01) | |
| *G16H 70/60* | (2018.01) | |
| *G06N 20/10* | (2019.01) | |
| *G06N 20/20* | (2019.01) | |
| *G06F 16/903* | (2019.01) | |
| *G06Q 10/06* | (2012.01) | |
| *G06N 5/02* | (2006.01) | |
| *G06N 20/00* | (2019.01) | |

(52) U.S. Cl.
CPC ............. *G06N 3/08* (2013.01); *G06N 20/10* (2019.01); *G16H 70/60* (2018.01); *G06F 16/90335* (2019.01); *G06N 5/02* (2013.01); *G06N 5/022* (2013.01); *G06N 5/025* (2013.01); *G06N 20/00* (2019.01); *G06N 20/20* (2019.01); *G06Q 10/0637* (2013.01)

(58) Field of Classification Search
CPC ............ G06N 3/02; G06N 5/02; G06N 5/022; G06N 5/025; G06N 5/04; G06N 5/045; G06N 3/08; G06N 20/00; G06N 20/10; G06N 20/20; G06F 16/90335; G06Q 10/0637; G16H 70/60
USPC ........................................ 706/11, 20, 21, 22
See application file for complete search history.

(56) References Cited

U.S. PATENT DOCUMENTS

| | | |
|---|---|---|
| 9,400,779 B2 | 7/2016 | Convertino et al. |
| 9,501,532 B2 | 11/2016 | Chen et al. |
| 9,507,854 B2 | 11/2016 | Brown et al. |

(Continued)

OTHER PUBLICATIONS

Agrawal, R. et al., Mining Newsgroups Using Networks Arising from Social Behavior, WWW (2003) May 20-24, Budapest, Hungary, 7 pages.

(Continued)

*Primary Examiner* — Shane D Woolwine
(74) *Attorney, Agent, or Firm* — Ortiz & Lopez, PLLC; Kermit D. Lopez; Luis M. Ortiz

(57) ABSTRACT

Method, system, and apparatus for automatic stance classification. Propositions can be collected that are relevant to a query. A classifier can classify the stance of each proposition based on whether the proposition supports the query, opposes the query, or is neutral with respect to the query in order to thereafter provide substantive data for decision making based on and extracted from the query. The stance can be classified based on, for example, an SVM-SC (SVM Based Stance Classification) approach and/or an NN-SC (Neural Network Stance Classification Approach).

20 Claims, 5 Drawing Sheets

(56) References Cited

U.S. PATENT DOCUMENTS

| | | | |
|---|---|---|---|
| 9,514,216 | B2 | 12/2016 | Duan et al. |
| 9,519,686 | B2 | 12/2016 | Bufe, III et al. |
| 9,519,713 | B2 | 12/2016 | Lotito |
| 2003/0018659 | A1 | 1/2003 | Fuks et al. |
| 2004/0220838 | A1* | 11/2004 | Bonissone ............ G06Q 40/08 705/4 |
| 2006/0036619 | A1 | 2/2006 | Fuerst et al. |
| 2008/0059391 | A1* | 3/2008 | Rosales ................. G06F 19/00 706/12 |
| 2009/0070322 | A1 | 3/2009 | Salvetti et al. |
| 2011/0153673 | A1 | 6/2011 | Boschee et al. |
| 2013/0103623 | A1* | 4/2013 | Burstein ............... G06N 20/00 706/12 |
| 2014/0172864 | A1 | 6/2014 | Shum |
| 2015/0112981 | A1* | 4/2015 | Conti .................... G06F 16/951 707/730 |
| 2015/0134694 | A1 | 5/2015 | Burke et al. |
| 2018/0197104 | A1* | 7/2018 | Marin ................... G06N 5/022 |

OTHER PUBLICATIONS

Agrawal, A. et al., Unsupervised Emotion Detection from Text using Semantic and Syntactic Relations, WI-IAT '12 Proceedings of the The 2012 IEEE/WIC/ACM International Joint Conferences on Web Intelligence and Intelligent Agent Technology—vol. 01, Dec. 4-7, 2012, pp. 346-353.

Anand, P. et al., Cats Rule and Dugs Drool!: Classifying Stance in Online Debate, Proceedings of the 2nd Workshop on Computational Approaches to Subjectivity and Sentiment Analysis (2011) Portland, OR, Jun. 24, 9 pages.

Balahur, A. et al., Determining the Polarity and Source of Pinions Expressed in Political Debates, Proceedings of the 10th International Conference on Computational Linguistics and Intelligent Text Processing (2009) Mexico City, Mexico, Mar. 1-7, pp. 468-480.

Bansal, M. et al., The power of negative thinking: Exploiting label disagreement in the min-cut classification framework, Coling 2008: Companion volume—Posters and Demonstrations (2008) Machester, pp. 15-18.

Biran, O. et al., Identifying Justifications in Written Dialogs, Proceedings of the 2011 IEEE Fifth International Conference on Semantic Computing (2011) Sep. 18-21, pp. 162-168.

Boltuzic, F. et al., Back up your Stance: Recognizing Arguments in Online Discussions, Proceedings of the First Workshop on Argumentation Mining (2014) Jun. 26, Baltimore, MD, pp. 49-58.

Burfoot, C. et al., Collective Classification of Congressional Floor-Debate Transcripts, Proceedings of the 49th Annual Meeting of the Associate for Computational Linguistics (2011) Portland, OR, Jun. 19-24, pp. 1506-1515.

Cohen, J., Weighted Kappa: Nominal Scale Agreement with Provision for Scaled Disagreement or Partial Credit, Pscyhological Bulletin (1968) 70(4):213-220.

Faulkner, A., Automated Classification of Stance in Student Essays: An Approach Using Stance Target Information and the Wikipedia Link-Based Measure, Proceedings of the Twenty-Seventh International Florida Artificial Intelligence Research Society Conference (2014) http://www.aaai.org/ocs/index.php/FLAIRS/FLAIRS14/paper/viewFile/7882/7820, 6 pages.

Ferreira, W. et al., Emergent: a novel data-set for stance classification, Proceedings of NAACL-HLT (2016) San Diego, CA, Jun. 12-17, pp. 1163-1168.

Hasan, K. S. et al., Stance Classification of Ideological Debates: Data, Models, Features, and Constraints, International Joint Conference on Natural Language Processing (2013) Nagoya, Japan, Oct. 14-18, pp. 1348-1356.

Malouf, R. et al., Taking sides: User classification for informal online political discourse, Internet Research (1008) 18(2):177-190.

Murakami, A. et al., Support or Oppose? Classifying Positions in Online Debates from Reply Activities and Opinion Expressions, Coling 2010: Poster Volume, Beijing, August, pp. 869-875.

Pado, S. et al., Design and realization of a modular architecture for textual entailment, Natural Language Engineering 21(2):167-200.

Rindflesch, T. C. et al., The interaction of domain knowledge and linguistic structure in natural language processing: interpreting hypemymic propositions in biomedical text, Journal of Biomedical Informatics (2003) 36:462-477.

Sobhani, P. et al., From Argumentation Mining to Stance Classification, Proceedings of the 2nd Workshop on Argumentation Mining (2015) Denver, CO, Jun. 4, pp. 67-77.

Somasundaran, S. et al., Recognizing Stances in Online Debates, Proceedings of the Joint Conference of the 47th Annual Meeting of the ACL and the 4th International Joint Conference on Natural Language Processing of the AFNLP (2009) Suntec, Singapore, Aug. 2-7, pp. 226-234.

Somasundaran, S. et al., Recognizing Stances in Ideological On-Line Debates, Proceedings of the NAACL HLT 2010 Workshop on Computational Approaches to Analysis and Generation of Emotion in Text, Los Angeles, CA, June, pp. 116-124.

Sridahar, D. et al., Collective Stance Classification of Posts in Online Debate Forums, ACL Joint Workshop on Social Dynamics and Personal Attributes in Social Media (2014) 9 pages.

Thomas, M. et al., Get out the vote: Determining support or opposition from Congressional floor-debate transcripts, Proceedings of EMLP (2006) pp. 327-335.

Walker, M. A. et al., Stance Classification using Dialogic Properties of Persuasion, 2012 Conference of the North American Chapter of the Association for Computational Linguistics: Human Language Technologies, Montreal, Canada, Jun. 3-8, pp. 592-596.

Wang, Y.-C. et al., Making Conversational Structure Explicit: Identification of Initiation-response Pairs within Online Discussions, Human Language Technologies: The 2010 Annual Conference of the North American Chapter of the ACL, Los Angeles, CA, June, pp. 673-676.

Yessenalina, A. et al., Multi-level Structured Models for Document-level Sentiment Classification, Proceedings of the 2010 Conference on Empirical Methods in Natural Language Processings, MIT, Massachusetts, Oct. 9-11, pp. 1046-1056.

* cited by examiner

| Can metabolic therapy cure brain cancer? ||
|---|---|
| Support | Oppose |
| Glucose is the primary fuel to cancer cells, hence low carb ketogenic diets can be effective in reducing growth of cancer cells in brain | Cancer is a genetic disease, hence cannot be impacted by any metabolic therapy |
| There are two specific patient narratives reported in literature, discussing specific ketogenic diets, which had led to remission of brain cancer | a Cochrane review found no significant evidence for the effectiveness of metabolic therapy in curing brain cancer |

FIG. 1

| Query | Support | Oppose | Neutral |
|---|---|---|---|
| E-cigarettes are safer than normal cigarettes (EC) | 93 | 165 | 155 |
| Sun exposure leads to skin cancer (SC) | 105 | 78 | 158 |
| Vitamin C prevents common cold (VC) | 111 | 68 | 99 |
| Women should take HRT post menopause (HR) | 42 | 136 | 68 |
| MMR vaccine can cause autism (MR) | 72 | 94 | 93 |

FIG. 2

| Example Sentence | Proposition | Local Stance Towards Proposition | Proposition Stance to Query | Overall Stance |
|---|---|---|---|---|
| There is considerable evidence that skin cancer occurs in those who have high sun exposure | Skin cancer occurs in those who have high sun exposure | Supports proposition | Supports | Supports |
| There is no evidence that skin cancer occurs in those who have high sun exposure | Skin cancer occurs in those who have high sun exposure | Opposes proposition | Supports | Opposes |
| Many studies have found that skin cancer rates are increasing in indoor workers | Skin cancer rates are increasing in indoor workers | Supports proposition | Opposes | Opposes |
| No reviews or research studies have determined that skin cancer rates are higher in indoor workers | Skin cancer rates are higher in indoor workers | Opposes proposition | Opposes | Supports |

FIG. 3

STANCE CLASSIFICATION OF MULTI-PERSPECTIVE CONSUMER HEALTH INFORMATION

TECHNICAL FIELD

Embodiments are generally related to the field of data mining. Embodiments also relate to the fields of text processing and stance classification. Embodiments additionally relate to health information mining.

BACKGROUND

With the rise of shared decision-making and the informed patient movement in healthcare, the World Wide Web (the "web" or "Web") is increasingly being utilized by consumers as an aid for health decision-making and the self-management of chronic illnesses. This is evidenced by the fact that one in every 20 searches on the Google search engine concerns health information. While the direct informational needs of Online Health Information Seekers regarding well-established disease symptoms and remedies are adequately met by general search engines such as Google, such search engines are not very effective in addressing complex consumer health queries, which do not provide for a single definitive answer.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide an improved data mining method, system, and apparatus/device.

It is another aspect of the disclosed embodiments to provide for methods, systems, and devices for automatic stance classification utilizing a stance classification framework.

It is yet another aspect of the disclosed embodiments to provide for an SVM-SC (SVM Based Stance Classification).

It is still another aspect of the disclosed embodiments to provide for the extraction of a textual entailment (TE) relation between a proposition and a query claim as in input to a classifier to address the semantic components of the disclosed stance classification framework.

The aforementioned aspects and other objectives and advantages can now be achieved as described herein. A method, system, and apparatus for automatic stance classification are disclosed. In an example embodiment, propositions can be collected that are relevant to a query (e.g., a medical query). A classifier can classify the stance of each proposition based on whether the proposition supports the query, opposes the query, or is neutral with respect to the query in order to thereafter provide substantive data for decision making based on and extracted from the query. The stance can be classified based on, for example, an SVM-SC (SVM Based Stance Classification) approach and/or an NN-SC (Neural Network Stance Classification Approach).

The disclosed embodiments provide for methods and systems for gleaning and classifying the medical stance regarding symptoms and treatment options for medical queries and their results online. Benefits of such embodiments include a means for interpreting a medical stance on symptoms and treatment options to provide substantive data for decision-making.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 1 illustrates a chart demonstrating a contradiction of search results for a clinical query;

FIG. 2 illustrates a chart demonstrating an example list of MPCHI queries;

FIG. 3 illustrates a chart demonstrating proposition and local stance annotations;

DETAILED DESCRIPTION

Figure 4:
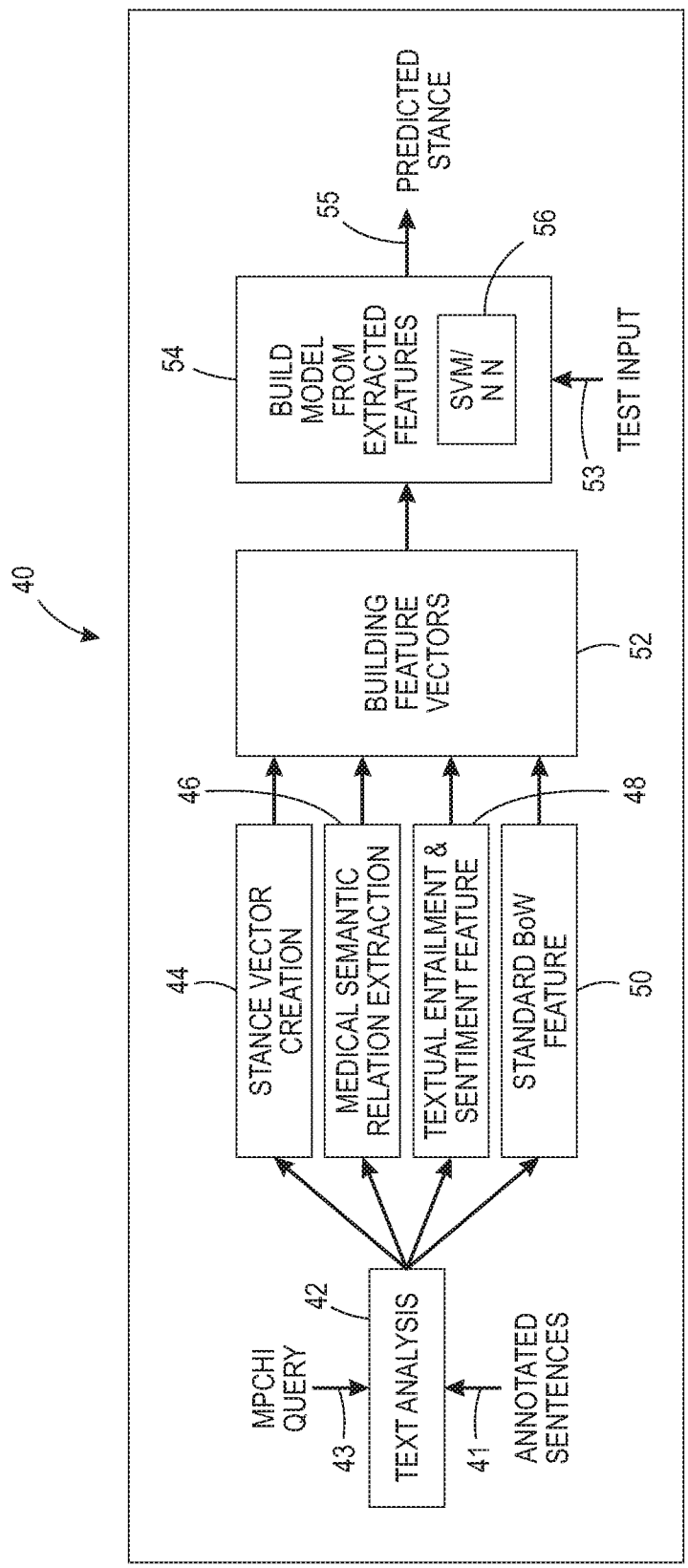
FIG. 4 illustrates a block diagram depicting a general architecture of a system for stance classification, in accordance with an example embodiment.

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware, or any combination thereof (other than software per se). The following detailed description is, therefore, not intended to be interpreted in a limiting sense.

Throughout the specification and claims, terms may have nuanced meanings suggested or implied in context beyond an explicitly stated meaning. Likewise, phrases such as "in one embodiment" or "in an example embodiment" and variations thereof as utilized herein do not necessarily refer to the same embodiment and the phrase "in another embodiment" or "in another example embodiment" and variations thereof as utilized herein may or may not necessarily refer to a different embodiment. It is intended, for example, that claimed subject matter include combinations of example embodiments in whole or in part.

In general, terminology may be understood, at least in part, from usage in context. For example, terms such as "and," "or," or "and/or" as used herein may include a variety of meanings that may depend, at least in part, upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures, or characteristics in a plural sense. Similarly, terms such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context. Additionally, the term "step" can be utilized interchangeably with "instruction" or "operation".

As indicated previously, the World Wide Web is increasingly being utilized by consumers as an aid for health decision-making and the self-management of chronic illnesses. This is evidenced by the fact that one in every 20 searches on the Google search engine concerns health information. While the direct informational needs of Online Health Information Seekers regarding well established disease symptoms and remedies are adequately met by general search engines such as Google, such search engines are not very effective in addressing complex consumer health queries, which do not have a single definitive answer. Consider the following two queries:

What are the symptoms of Diabetes?

Can metabolic therapy cure brain cancer?

While it is pretty straightforward to obtain an answer to the first query, retrieved results with respect to the second query above can result in considerable frustration for the searcher because now the searcher has to wade through hundreds of search results with contradictory views to obtain a balanced view of the evidence available. FIG. 1 illustrates a chart 10 that summarizes this scenario with few results to highlight the presence of both for and against views for the hypothesis posed in the search query. Note that the term Multi-Perspective Consumer Health Information (MPCHI) queries can be utilized to denote such queries, for which there is No Single Correct Answer; instead multiple and diverse perspectives (which very often are contradictory in nature) are available on the web regarding the queried information. The chart 10 shown in FIG. 1 thus demonstrates a contradiction of search results for an example clinical query. A header 12 labeled Support is shown at the top of the left hand column in FIG. 1, and a header 14 labeled Oppose is depicted at the of the right hand column in FIG. 1.

While the presentation of the multiple perspectives supporting and opposing the query as shown in FIG. 1 ideally makes it much easier for the user to consume the information, classifying the perspectives themselves to understand which perspectives are supporting the query proposition and which are opposing the query proposition took considerable effort even for a domain expert. This is due to multiple factors, which will be discussed herein. Layer users find it challenging to synthesize a balanced point of view even after spending considerable time navigating through the mass of results presented for such MPCHI queries. Helping the user to selectively make sense of the diverse perspectives available on the web, which can support or oppose his query proposition, is a crucial part of the role of search engines.

With concerns of life and death in balance, the presentation of correct and balanced information becomes crucial, as users would use the supporting and opposing information available to drive their decisions. While search engines have become extremely intelligent in retrieving diverse search results, which surfaces out the multiple perspectives pertinent to a query, currently they do not classify the returned perspectives so as to simplify the information consumption for end user. Given the increasing use of web by consumers for health and medical decision making, classifying the stance of the diverse perspectives which support and oppose the MPCHI query is a basic building block needed for any intelligent online health information system aimed at making available the collective intelligence of the web to online health information seekers.

Note that various other research challenges associated with MPCHI data mining render it a challenging research area. Such challenges include, for example, grading the supporting evidence for the perspectives, summarization, and effective presentation of perspectives to the searcher, just to mention a few. The disclosed embodiments thus focus on a specific task of stance classification of multi-perspective consumer health information.

Stance has been defined as the overall position towards an idea or proposition. There has been considerable research on stance classification in various domains such as political debates, online social media interactions, political news articles, etc. Some of these research efforts have been related to spoken conversations such as in Congressional Debate corpus. Other works on stance classification have focused on social media debate sites that contain user posts on a variety of topics. To date, however, there has not been any work that has looked at the stance classification of medical/health information. The medical domain makes this problem particularly more difficult due to various factors such as the fact that debates/posts on political/social topics are highly opinionated and contains considerable stance bearing cue words due to the passionate nature of the argumentative language used in such media.

The propositions which support/oppose each perspective are well demarcated and fixed in their stance position. For instance, consider the topic of legalizing abortion: a proposition such as freedom of choice is well entrenched in the pro-abortion stance whereas a proposition such as right to life is well entrenched in the anti-abortion stance. On the other hand, consider a proposition such as coffee enemas in metabolic therapy. It can be associated with supporting and opposing stance based on the evidence available, since MPCHI queries retrieve multiple diverse perspectives backed up by dynamically changing evidence available on the web. There is no clear-cut/black-white delineation of perspectives as supporting/opposing. The scientific language associated with these sentences presents these perspectives typically in a non-emotional, non-affective, neutral language, leading to a scarcity of sentiment/affect-bearing words. This is unlike other domains, where such sentiment/stance/affect bearing words are extensively used in user posts/debates and hence can serve as linguistic cues for stance classification. The technical language of the information in MPCHI queries is also another factor, which makes the stance classification complex. Given an example sentence E-cigarettes contain di-acetyl which has been associated with popcorn lung syndrome for a sample MPCHI query E-cigarettes are safer than normal cigarettes, it is not evident at first glance, whether this sentence is supportive/opposing the query. This makes the task more challenging compared to general domain stance classification.

Given the importance of MPCHI to online health information seekers, the disclosed embodiments focus on stance classification of MPCHI sentences. Given that MPCHI is a newly emerging area of research, unfortunately there are no existing datasets for stance classification of online consumer health information. In order to alleviate this need, a novel dataset of Multi-Perspective Consumer Health Information queries is presented herein. This example dataset is composed of five MPCHI queries and their associated sentences. These sentences were curated from the web search engine results retrieved in response to these queries. Each sentence is annotated with the stance information (supporting the query, opposing the query claim, neutral to the query claim). The annotation information also contains the proposition present in the sentence with respect to the query and the local stance towards the proposition in the sentence if any. The dataset is described in more detail herein.

The inherently different nature of MPCHI textual data brings forth the challenge that standard content based features used for typical stance detection settings alone do not suffice for MPCHI stance detection. This challenge can be overcome by extracting the underlying stance bearing characteristics of MPCHI text through a combination of rich set of features which include stance vector representation of sentences, the semantic medical relations, textual entailment relations in addition to the standard content based features according to the disclosed embodiments. Using these novel sets of extracted features, two design choice points can be evaluated in MPCHI stance classification techniques, one using Support Vector Machines classifier and another using neural networks. A detailed experimental evaluation of the dataset is disclosed herein with these approaches, which demonstrate that the disclosed techniques/embodiments are effective in stance classification of MPCHI.

The disclosed embodiments thus provide for the several major improvements. First, the problem of stance classification is introduced in the context of a novel environmental setting of multi-perspective consumer health information and a novel data set presented for this problem setting. Second, a novel set of features for MPCHI stance detection are disclosed, which include, for example, stance vectors, biomedical semantic relations, and textual entailment features. Such features can be used with the disclosed techniques for stance classification of MPCHI. More significantly, the disclosed embodiments highlight the need for greater research focus on the area of MPCHI, given the considerable research challenges and its beneficial impact on online health information seekers.

Given the absence of readily available corpus for multi-perspective consumer health information, a new data set for this category can be created from the web. Such a dataset can constitute a set of MPCHI queries and for each query, a set of relevant sentences can be provided, along with their stance classification. The stance classification is one of supports, opposes, or neutral with respect to the query. A set of MPCHI queries can be initially created, which is synthesized from real patient questions asked in online health forums. As mentioned before, these are consumer health information queries from which there is no definitive yes/no answer readily available, and multiple perspectives are present on the web, favoring and opposing the query claim with varying degrees of support. These are real burning questions, which many online consumer health information seekers are looking for information on. In addition, it may be desirable to consult with medical domain experts to validate that these are open queries in the sense that widely different perspectives exist in the medical community as well, with no single definitive answer. Out of these MPCHI queries, an example sub-set of five queries was selected for the dataset. A list of these example five queries is shown in column 1 of FIG. 2. That is, FIG. 2 illustrates a chart 20 demonstrating an example list of MPCHI queries. Note that column 1 in chart 20 of FIG. 2 is labeled with a header 22 designated as Query. Columns 2, 3, and 4 of chart 20 respectively are labeled with headers 24, 26, and 28 labeled respectively as Support, Oppose, and Neutral.

These queries (along with their paraphrase variations) can then be used as input to different search engines and a set of first 50 result links retrieved to these queries. The documents from these result links can be retrieved and the text cleaned up by removing ads, HTML tags, and other extraneous information via data cleaning scripts. A crowd sourced Human Intelligent Task (HIT) was run on Amazon's mechanical Turk platform, wherein each document was presented to 3 crowd workers who were asked to retrieve sentences relevant to the query from the document presented.

These results were then collated from the crowd sourced task using a majority vote for each sentence relevance and obtained a set of relevant sentences for each query. Extensive stance classification related annotation can then be performed on these sentences by means of human annotators. The annotation can include stance classification label for the whole sentence, the proposition contained in the sentence relevant to the query, the local stance type, and the local stance polarity towards the proposition. Each of these annotations is explained next.

FIG. 3 illustrates a chart 30 demonstrating proposition and local stance annotations. Five columns are shown in the chart 30 of FIG. 3, which from left to right are labeled with headers 32, 34, 36, 38, and 39, respectively, Example Sentence, Proposition, Local Stance Towards Proposition, Proposition Stance to Query, and Overall Stance. For each sentence, the stance classification is a label, which is one of supports, opposes, or neutral. The sentence can either contain a proposition relevant to the query as a constituent unit along with a local stance expression towards the proposition (as illustrated in FIG. 3) or the sentence as a whole itself can serve as the proposition relevant to the query. If the local stance towards the proposition is supportive, and the proposition itself supports the query claim, the overall stance for the sentence is supportive towards the query claim (e.g., see the example sentence 1 in chart 30 of FIG. 3). Similarly, if the local stance towards the proposition is opposing, and the proposition itself supports the query claim, then the sentence level stance will be opposing the query claim, as illustrated in sentence 2 in chart 30 of FIG. 3.

For these stance specific annotation of sentences, an annotation exercise can be performed in-house with human annotators. Each sentence can be annotated by at least three annotators and the annotation tags determined using majority voting and random tie breaking. An Inter-annotator agreement can be calculated using Cohen's Kappa. In this example it was found to be 0.82 for the sentence level stance annotation, which appears reasonable for tasks of this kind. The final annotation tags were reviewed and curated by a domain expert human annotator and only the sentences for which the domain expert annotator agreed with the majority of the human annotators were retained. The other sentences were discarded. These set of retained sentences constitute our data set, which contains totally 1541 sentences. Columns 2, 3, and 4 of FIG. 2 show the distribution of stance labels for each of the five queries in our data set. Our dataset has been made publicly available and can be accessed from the link https://sites.google.com/site/wsdmmpchidataset/.

Given a Multi-Perspective Consumer Health Information (MPCHI) query and a set of sentences/propositions retrieved as relevant sentences to that query, a challenge is to classify the stance of each given proposition as to whether it supports the query claim, opposes the query claim, or is neutral to the query claim. Note that the terms input sentence and input proposition can be used interchangeably herein, as the whole sentence itself might serve as the proposition or the proposition may be a constituent part of the sentence.

As discussed earlier, the language of MPCHI is considerably different from other typical stance detection corpus such as political/ideological debates due to its characteristics of sparsity of emotional/affective words, technical nature of the medical relations expressed, and the moderate toned scientific language used to convey the stance instead of passionate, opinionated language encountered in online social media debate forums. This inherently different nature of MPCHI textual data brings forth the challenge that standard content based features used for typical stance detection settings alone do not suffice for MPCHI stance detection. This challenge can be overcome in a novel fashion by extracting the underlying stance bearing characteristics of MPCHI text: (a) by extracting stance vectors which represent the stance content of each input sentence, by using annotated data and semantic relatedness measures; (b) by extracting and utilizing the medical semantic relations contained in the text; and (c) by considering the textual entailment relation between the input sentence and the MPCHI query. By combining these unique features along with standard content-based features, the disclosed embodiments offer two new approaches to stance detection of consumer health information text.

The first approach is based on the use of Support Vector Machines for classification using a novel combination of features. This first approach can be referred to as SVM based Stance Classification (SVM-SC). The second approach is based on the use of a neural network for MPCHI stance classification, which can be referred to as NN-SC. While these are independent approaches, exploring two totally different design choice points among a wide spectrum of techniques available for stance detection in text, they follow the general architecture shown in FIG. 4, which can also be used for NLP/machine learning based approaches for stance detection. The methods for extracting the novel characteristics of MPCHI text are initially discussed followed by a description of the two stance detection approaches.

FIG. 4 illustrates a block diagram depicting a general architecture of a system 40 for stance classification, in accordance with an example embodiment. The system 40 shown in FIG. 4 includes a text analysis module 42, which receives data indicative of annotated sentences 41 and an MPCHI query 43. Data output from the text analysis module 42 can be subject to modules 44, 46, 48, and 50 which respectively process operations involving stance vector creation, medical semantic relation extraction, textual entailment and sentiment feature, and a standard BoW feature. Data from modules 44, 46, 48, and 50 can then be provided to a module 52 for building feature vectors. Output from module 52 is then provided to a module 54 that builds a model from the extracted features. Test input data 52 can also be provided to module 54. The module 54 can include an SVM/NN module 56. The output from module 54 thus generates a predicted stance 55.

Figure 5:
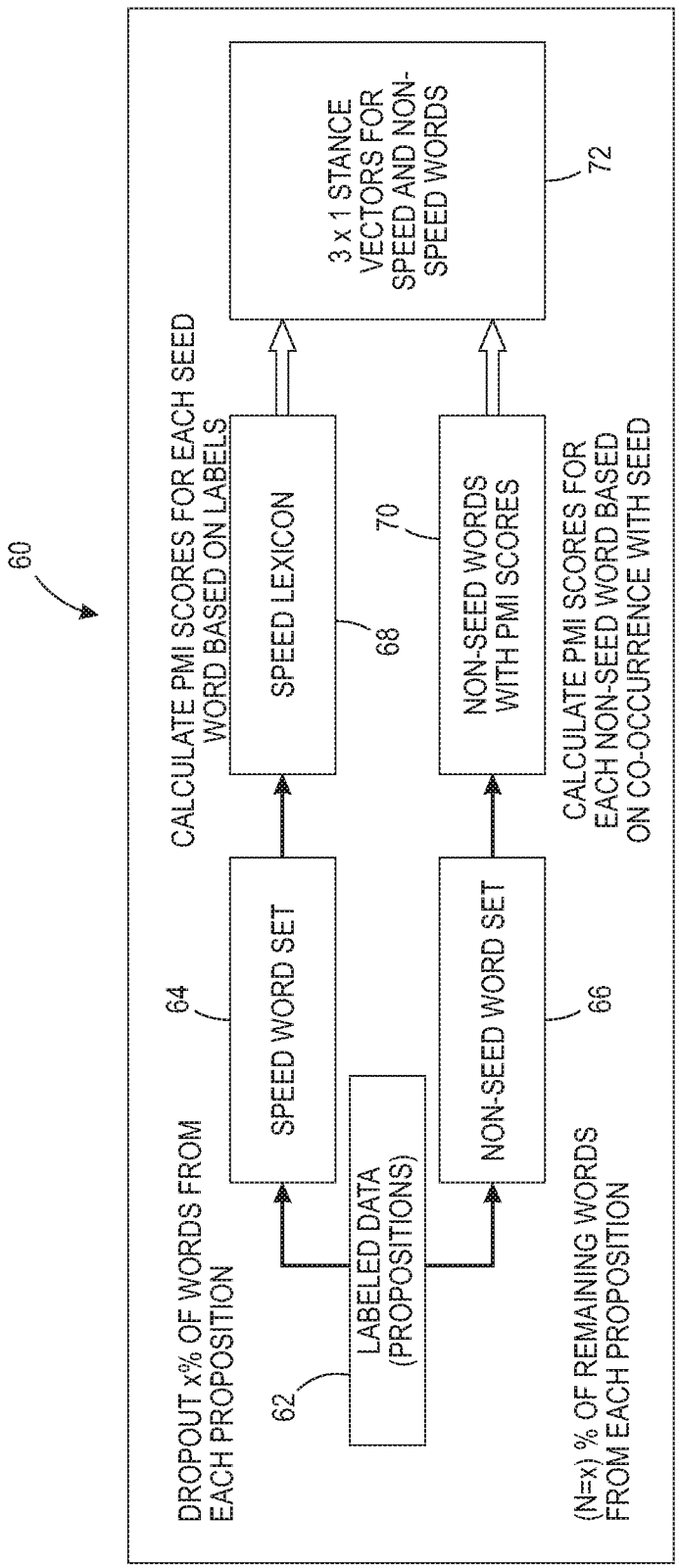
FIG. 5 illustrates a flow chart of operations depicting logical operational steps of a method for stance vector extraction, in accordance with an example embodiment.

FIG. 5 illustrates a flow chart of operations depicting logical operational steps of a method 60 for stance vector extraction, in accordance with an example embodiment. As shown at block 62, an operation can be implemented with labeled data (propositions) provided. This data can then be subject to a seed word set operation as shown at block 64 and a non-seed word set operation as depicted at block 66. Following processing of the seed word set operation indicated at block 64, a seed lexicon is then generated as shown at block 68, followed by an operation involving a 3×1 stance vectors for seed and non-seed words, as depicted at block 72. Regarding the operation shown at block 68, PMI scores can be calculated for each seed word based labels. Following processing of the operation indicated at block 66 (i.e., the non-seed word set), an operation can be implemented to provide non-seed words with PMI scores, as shown at block 70. Note that the PMI scores are calculated for each non-seed word based on co-occurrence with seeds. Following processing of the operation depicted at block 70, the operation indicated at block 72 can be processed.

Word level stance vectors are vector representations of the stance content of the text. Certain types of words in text typically carry stance and these are the Noun, Adjective, Verb, and Adverb (NAVA) words. Hence, the stance associated with each sentence is in turn attributed to the NAVA words present in the sentence. The disclosed approach of stance vector generation can in some embodiments involve the use of unsupervised emotion detection and can be summarized as follows: first, using a fraction of annotated labeled data, stance vectors are created for a seed set of NAVA words and this forms the stance seed lexicon. A stance representative seed lexicon is basically a mapping of each NAVA seed word (except the standard stop words) to its dominant stance in the dataset.

Stance vectors for seed words can be constructed by measuring the alignment of each NAVA seed word towards the three stance categories of support, oppose, and neutral. It then extracts the other stance bearing NAVA words in the corpus (the non-seed set) and creates the word level stance vectors for these non-seed words by computing their semantic relatedness to the stance representative words in the seed stance lexicon. It then computes the stance corresponding to each sentence by aggregating the word-wise stance vectors obtained. The overall block diagram demonstrating a methodology of stance vector extraction is shown in FIG. 5.

The steps involved in stance vector extraction are explained next as follows. First, the propositions are POS-tagged to extract the NAVA words. Then, a fraction of these NAVA words can be used from each proposition to construct the seed stance lexicon from the corpus. The remaining NAVA words belonging to each proposition in the whole corpus (non-seed data) form the non-seed set. For each NAVA word in the seed set, we calculate the PointWise Mutual Information (PMI) of the seed word with respect to the three stance classes (using the ground truth labels of the propositions). PMI is an information theoretic measure of semantic relatedness based on probability of co-occurrence. The co-occurrence of each seed word with each specific stance class can be measured using ground truth labels of the seed data and compute the PMI scores of each seed word with respect to each of the stance classes. These three PMI scores together form the stance vector for this seed word. Also, this word can be mapped to the stance class that has the maximum PMI score with respect to the word. For example, if the word 'causes' has the maximum score with respect to the support class, this word is mapped to the support class. In other words, 'causes' now becomes a seed word for the support class. In a similar fashion, all words in the seed set can be mapped to their corresponding stance classes to form the seed lexicon (using their PMI based stance vectors). This step completes the formation of the seed lexicon, at the end of which are stance vectors constructed for each seed word associated with a specific stance class.

Next, the stance vectors for the words in the non-seed set can be computed for which we do not know the stance alignment (note that for these words, the use of the ground truth labels for the vector generation can be deliberately avoided). For this, the PMI of each nonseed word can be calculated with respect to each seed word based on the co-occurrence count of the word pair in the entire corpus. Now, for each non-seed word, the stance score can be calculated with respect to a particular stance class as the geometric mean of the PMIs of that non-seed word with respect to all seed words belonging to that stance class. Geometric mean is used as it captures the central tendency well enough. For example, if the stance class support contains the seed words a, b, c, and d is a non-seed word, then:

score($d$,support)=GM(PMI($d,a$),PMI($d,b$),PMI($d,c$))

where GM stands for Geometric Mean and the PMIs are based on co-occurrence (in the same proposition) counts of (d,a), (d,b), and (d,c) pairs in the proposition dataset. Thus, each non-seed word now gets a three-dimensional stance vector similar to the seed words. Finally, these stance vectors (for both seed and non-seed words) can be used to derive a sentence level stance vector by simply taking the mean of the stance vectors of all words present in the sentence, which can then be used as an input feature to the classifier along with other feature vectors.

The rationale behind dividing the NAVA words in the corpus into seed and non-seed sets (and not using the ground truth labels to obtain stance vectors for the non-seed words) is based on assuming a real world setting while devising this approach. In the present case, the complete dataset can be labeled. However, in a real time system, we might come across new, unlabeled data (propositions or sentences), for which stance vector calculation has to be done. Our process of co-occurrence based stance vector generation for unfamiliar words leverages the intuition that at least in a homogeneous dataset (containing data on similar issues), if two words co-occur frequently, there is a high likelihood that their stance alignments will be similar. Thus, even for unlabeled data, our semi-supervised approach of stance vector generation can aid in generating stance vector representations.

It should also be noted that while the disclosed embodiments involve a stance vector representation motivated in part from an unsupervised emotion detection approach, the underlying approaches themselves are quite different. That is, other work has been involved in a totally unsupervised setting, wherein emotion representative initial seed words needed to be provided manually for each emotion category using which seed emotion vectors are constructed. In the disclosed embodiments, however, a fraction of labeled annotated data is used for creating the seed lexicon. Also, the disclosed embodiments use generated stance vector representations as feature vectors to a classifier instead of using them directly as a stance label for each input sentence.

While stance vectors capture the attribution of the constituent stance bearing words of the sentence to the overall stance towards the MPCHI query claim, another equally important characteristic of MPCHI text is the fact that they often contain medical semantic relations and these relations are an implicit indicator of the stance of the sentence towards the query claim. For example, consider the sentence high sun exposure is shown to further increase the risk of melanoma retrieved in relation to the query Sun exposure causes skin cancer.

This sentence contains the medical semantic relation pre-disposes which represents the fact sun exposure is a causative factor towards the disease melanoma, thereby implicitly supporting the query claim of sun light causing skin cancer. There are a number of medical semantic relations such as TREATS which is used to associate a substance to the disease it treats, PREVENTS which is used to associate a substance to a disease/condition it prevents from occurring, CAUSES which is used to associate a causative factor to a disease-condition, etc. These relations, which are present in the sentence can serve as implicit cues towards the stance of the sentence. Hence, it makes sense to extract these biomedical semantic relations and feed them as input features to the MPCHI stance classifiers.

SemRep from the National Library of Medicine is a tool for extracting biomedical semantic predications. The UMLS Metathesaurus, the largest thesaurus in the biomedical domain, provides a representation of biomedical knowledge consisting of concepts classified by semantic type and both hierarchical and non-hierarchical relationships among the concepts. SemRep uses domain knowledge provided by the UMLS Metathesaurus to represent the textual content as semantic predication.

For example, SemRep extracts the predication Infection-CAUSES-Guillain-Barre Syndrome from the sentence Infections can trigger GBS. For the disclosed MPCHI query, two meta relations can be created namely disease-causing and disease-treating which aggregate relevant SemRep predications for these two categories. In some example embodiments, SempRep can be used to extract the biomedical semantic predications from the sentences and mapped them to the two meta-relations of our interest. The presence of these two meta-relations in the input sentences can be mapped to a 2-bit binary vector, which is then fed as part of the feature vector to the classifier.

The discussion now turns to the extraction of textual entailment relations. While stance vectors serve as a means of representing the stance content of constituent words, and semantic medical relations represent the implicit domain specific relational content of the sentences, capturing the overall semantic relationship of the proposition and the query claim is essential in modeling the stance of the proposition towards the query claim. If it can be established that the query claim can be inferred from the proposition, then the proposition is supporting the query claim, whereas if it contradicts the query claim, then it is not supporting the query claim. Such higher order inference relations between pairs of sentences are expressed through the linguistic relationship of textual entailment (TE). TE is a directional relation between text fragments. The relation holds whenever the truth of one text fragment follows from another text. In the TE framework, the entailing and entailed texts are termed text (T) and hypothesis (H), respectively. T entails H if the meaning of H can be inferred from the meaning of T, as would typically be interpreted by people. Hence, using the TE relation between the proposition and query claim as an input to the classifier addresses the semantic component of our stance classification modeling framework.

Towards this end, an EOP (Excitement Open Platform) can be used, which supports a rich set of Textual Entailment Decision Algorithms. EOP supports different pre-trained Entailment Decision Algorithms, some of which are purely syntactic feature based and some others, which also utilize external linguistic resources such as WordNet, VerbOccean. In some example embodiments, two TE algorithms can be utilized, one from each of these two categories, namely MaxEntClassificationEDA-Base+WN+VO+TP+TPPos+TS and EditDistanceBase-EN, to compute the textual entailment relation between the proposition in the input sentence and the query claim. The results can be represented as a two-bit feature vector, which can be presented as input to the stance classifier.

In addition, standard content features can be employed using a Bag of Words feature representation as part of the input to the classifier. This can be augmented with sentiment polarity of each proposition. The sentiment analysis engine available in the Stanford CoreNLP toolkit can be used, for example, in some embodiments, and the output label mapped to one of three classes, namely positive, negative, and neutral. Given that a number of different design choice points are possible for the stance classifier, in some embodiments, the focus may be on two representative choice points by using a SVM classifier in the discussed first approach and a Neural Network based classifier in the discussed second approach.

In an SVM-SC approach, stance classification can be modeled as a 3-class classification problem using Support Vector Machines as the classifier and taking as input a rich set of features covering the proposition stance vectors, biomedical relations present in the proposition, semantic textual entailment relations between the proposition and the query claim, in addition to the standard content based features such as Bag of Word features and sentiment polarity of the proposition. The approach can be termed a Feature Rich Stance Classification (SVM-SC) method. In some example embodiments, a linear kernel SVM of type C-SVC can be used, with default parameter values of, for example, C=1 and a 10 fold cross-validation.

In an NN-SC approach, a general three layer neural network (NN) can be utilized to predict the stance category of each input sentence (proposition) for an MPCHI query. The input to the network is a (d×s) matrix, where d is the maximum number of features across all combinations and s is the dimensionality. This size can be kept fixed and zero padding used whenever required. In this example scenario, the size of the output layer is 3 units (corresponding to the 3 stance labels) and the hidden layer is of, for example, size 200 units. The Adam update algorithm can be used with a cross-entropy loss function to train the neural network with an initial learning rate of, for example, 0:001. The Softmax activation function can be used in the output layer for the prediction of the stance labels. A dropout value of 0.5 can be used in the softmax layer (to avoid overfitting) and a mini-batch size of 50. It is not necessary to otherwise perform any dataset specific tuning of the neural network. A detailed experimental evaluation of the discussed two approaches is disclosed in the next section.

As mentioned before, since there are no readily available data sets for MPCHI stance detection setting, a new data set can be created for this task. The data set can be composed of, for example, five MPCHI queries with each query having A, B, C, D, and E sentences respectively. In this section, experimental results are reported for the two MPCHI stance detection schemes—the SVM-SC and NN-SC approaches.

TABLE 1

Results for SVM-SC Approach

| SVM | EC | SC | VC | HRT | MMR | AVG |
|---|---|---|---|---|---|---|
| BOW | 58.66 | 53.69 | 58.63 | 63.82 | 66.79 | 60.32 |
| STA | 86.92 | 81.71 | 79.14 | 85.77 | 87.64 | 84.24 |
| ENT | 37.29 | 47.19 | 40.65 | 55.28 | 43.24 | 44.73 |
| BOW + ENT | 58.84 | 58.41 | 59.35 | 59.76 | 64.48 | 60.17 |
| BOW + STA | 70.70 | 68.73 | 67.63 | 67.48 | 76.06 | 70.12 |
| STA + ENT | 86.68 | 80.83 | 79.50 | 84.15 | 88.80 | 83.99 |
| BOW + STA + ENT | 70.94 | 69.32 | 68.71 | 67.48 | 74.52 | 70.19 |
| SENTI | 40.68 | 46.61 | 41.01 | 55.28 | 40.93 | 44.90 |
| SENTI + MED | 48.91 | 58.41 | 44.24 | 58.13 | 47.10 | 51.36 |
| STA + SENTI | 86.68 | 78.76 | 79.14 | 83.74 | 87.64 | 83.19 |
| STA + SENTI + MED | 84.50 | 82.01 | 80.58 | 85.77 | 87.64 | 84.10 |
| ALL (EXCEPT BOW) | 84.26 | 82.01 | 78.78 | 84.55 | 88.41 | 83.60 |

As mentioned earlier, the nature of MPCHI text brought forth the need for a rich and novel set of features to be extracted from it for effective stance detection. The feature set includes stance vectors (STA), semantic medical relations (MED), textual entailment (ENT), Sentiment (SENTI) in addition to the regular Bag of Words (BOW) features. Both approaches have been evaluated for different combination of these features. Sample results of experiments for our first approach SVM-SC are reported in Table 1 and sample results for the second approach NN-SC are shown in Table 2.

Columns 2 to 6 of the Table 1 presents the accuracies for each of the five MPCHI queries individually and Column 7 of the Table 1 presents the average query accuracy for our first approach for each of the different feature set combination. With the SVM-SC approach, we find that stance vectors as input features outperform all other feature set combinations in terms of the average query accuracy, achieving an average query accuracy of 84:24%. In fact, we find that stance vectors yield the best accuracy for 3 of the queries. In the remaining two queries, its performance difference with the best achieved accuracy is negligibly small. The feature set combination of stance vectors along with sentiment feature and semantic medical relations feature achieves the best accuracy for three of the queries (though its performance delta over stance vector alone is quite small). Our current set of experiments with SVM-SC indicate that although MPCHI text lends itself to extracting rich set of features from it, stance vectors on their own serve as a good representation for the stance bearing constituent words of the input sentences. This seems to suggest that other set of features, which we had used in our experiments may not be necessary for effective stance classification of MPCHI text. However, these results have to be taken with the strong caveat that our current data set of MPCHI queries is not very large, and hence this conclusion needs to be validated with larger MPCHI data sets. Over the coming month, we plan to release a larger dataset (doubling the size of our current data set) and validate these initial conclusions.

TABLE 2

Results for NN-SC Approach

| NN | EC | SC | VC | HRT | MMR | AVG |
|---|---|---|---|---|---|---|
| STA | 86.99 | 82.33 | 80.00 | 86.49 | 89.99 | 85.16 |
| STA +SENTI | 85.50 | 83.67 | 82.49 | 84.49 | 88.49 | 84.93 |
| STA + MED | 87.25 | 83.33 | 80.99 | 85.00 | 88.99 | 85.11 |

TABLE 2-continued

Results for NN-SC Approach

| NN | EC | SC | VC | HRT | MMR | AVG |
|---|---|---|---|---|---|---|
| STA + SENTI + MED | 86.49 | 86.67 | 83.50 | 86.49 | 87.99 | 86.23 |
| BOW + STA + ENT | 77.25 | 70.67 | 73.99 | 65.50 | 63.50 | 70.18 |
| ALL (EXCEPT BOW) | 82.25 | 83.99 | 73.99 | 84.99 | 85.49 | 82.14 |

Columns 2 to 6 of the Table 2 presents the 10-fold cross validation accuracies for each of the five MPCHI queries individually and Column 7 of the Table 2 presents the average query accuracy for our second approach for each of the different feature set combinations. The mappings of abbreviated query names used in Table 1 and Table 2 to their full query sentences are described in the column 1 of FIG. 2.

The feature set combination of stance vectors, semantic medical relations and sentiment (STA+MED+SENTI) achieves the best average accuracy across all combinations, achieving an accuracy of 86.23%. As seen with SVM-SC approach, stance vectors alone outperform most of the feature vector combinations, achieving an average accuracy of 85.16% which is very close to the best average accuracy of 86.23% achieved with (STA+MED+SENTI). We find that the best average accuracy achieved by NN-SC approach is slightly better than that of SVM-SC approach (86.23% compared to 84.24%). Given that we use a simpler neural network structure, this seems to indicate that the nature of neural network classifier allows it to learn certain features inherently which enables it to outperform the SVM classifier. The results reported in Table 1 and Table 2 is with the value of seed data fraction threshold value equal to 0.75 (the percentage of NAVA words in each proposition used to form the seed set). We also repeated the above experiments with the seed data fraction threshold equal to 0.5. We found the average query accuracy (for the best feature set combination of STA+MED+SENTI) in the case of SVM-SC to be 80.89% and 81.4% for the NN-SSC approach, indicating that stance vector representation generalizes quite well across different seed lexicon data sizes, and that the performance does not degrade much despite having 50% of the proposition words as non-seed words (for which we do not use the ground truth to calculate the stance vectors).

As described herein, the mean of the stance vectors of the individual words in the sentence can be taken to represent the sentence level stance vectors for our input sentences and fed them as input feature vectors to the classifier. Since it is also possible to feed the word level stance vectors to the neural network as a multi-dimensional matrix (instead of taking the mean of the constituent word vectors), the present inventors also experimented with the same. However, we found that the average query accuracy (for the best feature set combination) drops to 79.1%. This is possibly due to the low dimensional (e.g., 3×1) embedding representation of the stance vectors for the individual words. Instead, for the experiments discussed herein, the present inventors followed the approach of representing the sentence level stance feature vector as the mean of the stance vectors of the constituent words.

In the discussed example experimental evaluation, cross-query experiments were not performed using first query's input sentences to train the model and testing the model with the second query's input sentences. This was intentional due to the fact that vocabulary overlap across input sentences of different queries was less than 20% (after removal of stop words and grouping of the words into different semantic categories) indicating the non-overlapping nature of the content. Given this highly non-overlapping nature of inputs across queries, and the fact that our approaches are driven by the underlying linguistic content of the input sentences, it did not make sense to perform cross-query training.

Embodiments are thus disclosed, which address the problem of stance detection in the novel setting of multi-perspective consumer health information queries. Given the novel problem context and the absence of any existing datasets for this problem context, a new data set is developed and evaluated the same with two different stance classification schemes. Given the sparsity of stance-bearing/effective language in MPCHI text, the disclosed novel approach uses stance vectors to extract and represent the underlying stance bearing characteristics of MPCHI text.

The present inventors have experimented with a rich set of non-traditional features such as medical semantic relations, textual entailment, and sentiment in conjunction with stance vectors. Feeding these diverse feature set combinations to the disclosed two stance classification approaches, the inventors were able to achieve an average accuracy of 84.24% for the first approach and 86.23% for the second approach. Experimental results indicate that stance vectors based classification outperforms all other feature set combinations in almost all cases and hence can serve as a good representation of the stance bearing MPCHI text. The present inventors plan to release a larger dataset (doubling the size of our current data set) and validate these initial conclusions with the larger data set. The disclosed stance vector based approach is able to perform well for different proportions of seed data set, indicating its ability to generalize well.

The disclosed embodiments can help to focus the attention of the WSDM research community towards the problem of MPCHI search and mining. Finally, it is anticipated that a complete end to end system will be developed based on the disclosed embodiments, which can classify the multiple perspectives, summarize, and provide a balanced point of view presentation. The disclosed embodiments are a first step in this direction.

As can be appreciated by one skilled in the art, embodiments can be implemented in the context of a method, data processing system, or computer program product. Accordingly, embodiments may take the form of an entire hardware embodiment, an entire software embodiment, or an embodiment combining software and hardware aspects all generally referred to herein as a "circuit" or "module." Furthermore, embodiments may in some cases take the form of a computer program product on a computer-usable storage medium having computer-usable program code embodied in the medium. Any suitable computer readable medium may be utilized including hard disks, USB Flash Drives, DVDs, CD-ROMs, optical storage devices, magnetic storage devices, server storage, databases, etc.

Computer program code for carrying out operations of the present invention may be written in an object oriented programming language (e.g., Java, C++, etc.). The computer program code, however, for carrying out operations of particular embodiments may also be written in conventional procedural programming languages, such as the "C" programming language or in a visually oriented programming environment, such as, for example, Visual Basic.

The program code may execute entirely on the user's computer, partly on the user's computer, as a stand-alone software package, partly on the user's computer and partly on a remote computer, or entirely on the remote computer. In the latter scenario, the remote computer may be connected to a user's computer through a local area network (LAN) or a wide area network (WAN), wireless data network e.g., Wi-Fi, Wimax, 802.xx, and cellular network or the connection may be made to an external computer via most third party supported networks (for example, through the Internet utilizing an Internet Service Provider).

The embodiments are described at least in part herein with reference to flowchart illustrations and/or block diagrams of methods, systems, and computer program products and data structures according to embodiments of the invention. It will be understood that each block of the illustrations, and combinations of blocks, can be implemented by computer program instructions. These computer program instructions may be provided to a processor of, for example, a general-purpose computer, special-purpose computer, or other programmable data processing apparatus to produce a machine, such that the instructions, which execute via the processor of the computer or other programmable data processing apparatus, create means for implementing the functions/acts specified in the block or blocks. To be clear, the disclosed embodiments can be implemented in the context of, for example, a special-purpose computer or a general-purpose computer, or other programmable data processing apparatus or system. For example, in some embodiments, a data processing apparatus or system can be implemented as a combination of a special-purpose computer and a general-purpose computer.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the various block or blocks, flowcharts, and other architecture illustrated and described herein.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
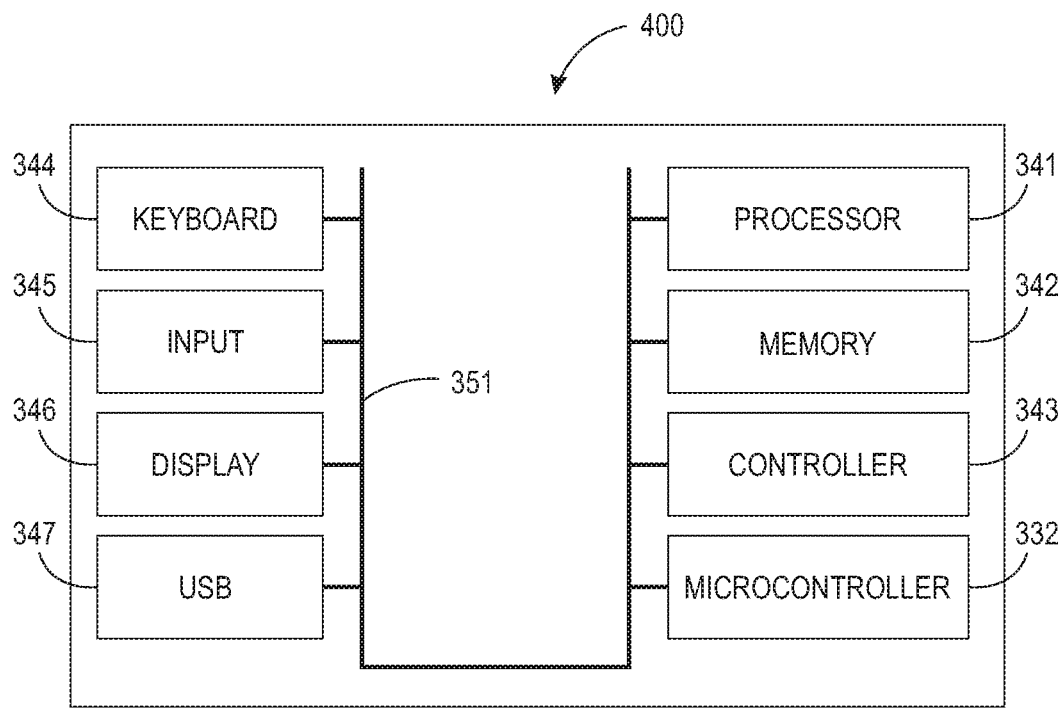
FIG. 6 illustrates a schematic view of a computer system, in accordance with an embodiment.
Figure 7:
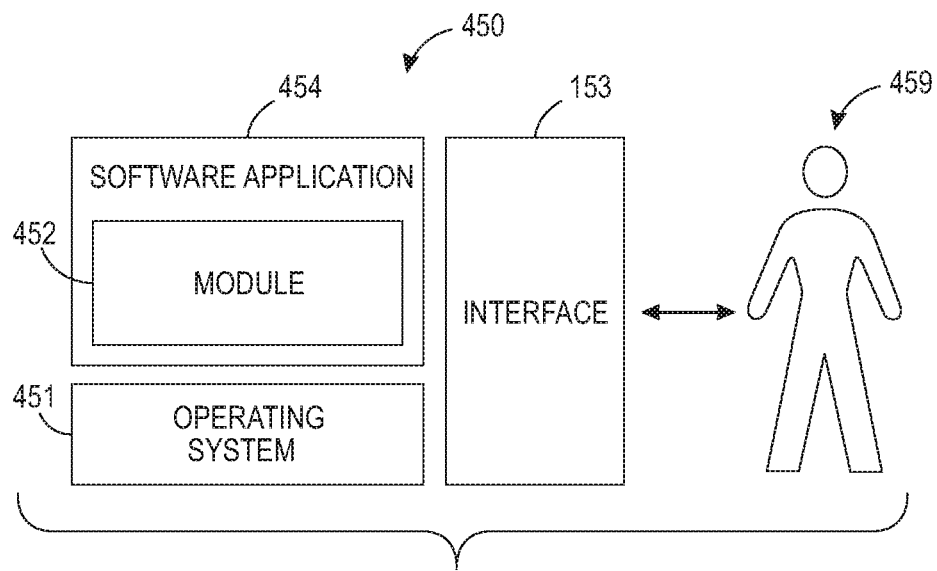
FIG. 7 illustrates a schematic view of a software system including a module, an operating system, and a user interface, in accordance with an embodiment.

FIGS. 6-7 are shown only as exemplary diagrams of data-processing environments in which example embodiments may be implemented. It should be appreciated that FIGS. 6-7 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

As illustrated in FIG. 6, some embodiments may be implemented in the context of a data-processing system 400 that can include, for example, one or more processors such as a processor 341 (e.g., a CPU (Central Processing Unit) and/or other microprocessors), a memory 342, an input/output controller 343, a microcontroller 332, a peripheral USB (Universal Serial Bus) connection 347, a keyboard 344 and/or another input device 345 (e.g., a pointing device, such as a mouse, track ball, pen device, etc.), a display 346 (e.g., a monitor, touch screen display, etc.) and/or other peripheral connections and components.

As illustrated, the various components of data-processing system 400 can communicate electronically through a system bus 351 or similar architecture. The system bus 351 may be, for example, a subsystem that transfers data between, for example, computer components within data-processing system 400 or to and from other data-processing devices, components, computers, etc. The data-processing system 400 may be implemented in some embodiments as, for example, a server in a client-server based network (e.g., the Internet) or in the context of a client and a server (i.e., where aspects are practiced on the client and the server).

In some example embodiments, data-processing system 400 may be, for example, a standalone desktop computer, a laptop computer, a Smartphone, a pad computing device, and so on, wherein each such device is operably connected to and/or in communication with a client-server based network or other types of networks (e.g., cellular networks, Wi-Fi, etc.).

FIG. 7 illustrates a computer software system 450 for directing the operation of the data-processing system 400 depicted in FIG. 6. The software application 454, stored for example, in memory 342, can include a module 452. The computer software system 450 can also include a kernel or operating system 451 and a shell or interface 453. One or more application programs, such as software application 454, may be "loaded" (i.e., transferred from, for example, mass storage or another memory location into the memory 342) for execution by the data-processing system 400. The data-processing system 400 can receive user commands and data through the interface 453; these inputs may then be acted upon by the data-processing system 400 in accordance with instructions from operating system 451 and/or software application 454. The interface 453 in some embodiments can serve to display results, whereupon a user 459 may supply additional inputs or terminate a session. The software application 454 can include the module(s) 452, which can, for example, implement instructions or operations such as those discussed herein with respect to FIG. 4-5 herein. Module 452 may also be composed of a group of modules, such as modules 42, 44, 46, 48, 50, 52, 54 (and module 56) shown in FIG. 4. The module 452 can be configured, for example, to implement instructions such as those described herein with respect to blocks 62, 64, 66, 68, 70, and 72 shown in FIG. 5.

The following discussion is intended to provide a brief, general description of suitable computing environments in which the system and method may be implemented.

Although not required, the disclosed embodiments will be described in the general context of computer-executable instructions, such as program modules being executed by a single computer. In most instances, a "module" can constitute a software application, but can also be implemented as both software and hardware (i.e., a combination of software and hardware).

Generally, program modules include, but are not limited to, routines, subroutines, software applications, programs, objects, components, data structures, etc., that perform particular tasks or implement particular data types and instructions. Moreover, those skilled in the art will appreciate that the disclosed method and system may be practiced with other computer system configurations, such as, for example, hand-held devices, multi-processor systems, data networks, microprocessor-based or programmable consumer electronics, networked PCs, minicomputers, mainframe computers, servers, and the like.

Note that the term module as utilized herein may refer to a collection of routines and data structures that perform a particular task or implements a particular data type. Modules may be composed of two parts: an interface, which lists the constants, data types, variable, and routines that can be accessed by other modules or routines; and an implementation, which is typically private (accessible only to that module) and which includes source code that actually implements the routines in the module. The term module may also simply refer to an application, such as a computer program designed to assist in the performance of a specific task, such as word processing, accounting, inventory management, etc.

FIGS. 6-7 are thus intended as examples and not as architectural limitations of disclosed embodiments. Additionally, such embodiments are not limited to any particular application or computing or data processing environment. Instead, those skilled in the art will appreciate that the disclosed approach may be advantageously applied to a variety of systems and application software. Moreover, the disclosed embodiments can be embodied on a variety of different computing platforms, including Macintosh, UNIX, LINUX, and the like.

The claims, description, and drawings of this application may describe one or more of the instant technologies in operational/functional language, for example, as a set of operations to be performed by a computer. Such operational/functional description in most instances can be specifically-configured hardware (e.g., because a general purpose computer in effect becomes a special-purpose computer once it is programmed to perform particular functions pursuant to instructions from program software). Note that the data-processing system 400 discussed herein may be implemented as special-purpose computer in some example embodiments. In some example embodiments, the data-processing system 400 can be programmed to perform the aforementioned particular instructions thereby becoming in effect a special-purpose computer.

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein can be a distillation of machine specifications or other physical mechanisms specified by the operations/functions such that the otherwise inscrutable machine specifications may be comprehensible to the human mind. The distillation also allows one skilled in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions are representative of static or sequenced specifications of various hardware elements. This is true because tools available to implement technical disclosures set forth in operational/functional formats—tools in the form of a high-level programming language (e.g., C, java, visual basic, etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. In order to facilitate human comprehension, in many instances, high-level programming languages resemble or even share symbols with natural languages.

It has been argued that because high-level programming languages use strong abstraction (e.g., that they may resemble or share symbols with natural languages), they are therefore a "purely mental construct." (e.g., that "software"—a computer program or computer programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In an example embodiment, if a high-level programming language is the tool used to implement a technical disclosure in the form of functions/operations, it can be understood that, far from being abstract, imprecise, "fuzzy," or "mental" in any significant semantic sense, such a tool is instead a near incomprehensibly precise sequential specification of specific computational—machines—the parts of which are built up by activating/selecting such parts from typically more general computational machines over time (e.g., docked time). This fact is sometimes obscured by the superficial similarities between high-level programming languages and natural languages. These superficial similarities may also cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory devices, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors).

The logic circuits forming the microprocessor are arranged to provide a micro architecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output.

The Instruction Set Architecture includes a specification of the machine language that can be used by programmers to use/control the microprocessor. Since the machine language instructions are such that they may be executed directly by the microprocessor, typically they consist of strings of binary digits or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second).

Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification, which selects out hardware logic gates, specifies voltage levels, voltage transition timings, etc., such that the humanly useful work is accomplished by the hardware.

Thus, a functional/operational technical description, when viewed by one skilled in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. Accordingly, any such operational/functional technical descriptions may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object, which has a stable, measurable, and changeable state may be used to construct a machine based on the above technical description. Charles Babbage, for example, constructed the first computer out of wood and powered by cranking a handle.

Thus, far from being understood as an abstract idea, it can be recognized that a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc., with natural language simply cannot be taken as an indication that such functional/operational technical descriptions are abstract ideas or mere expressions of abstract ideas. In fact, as outlined herein, in the technological arts this is simply not true. When viewed through the tools available to those skilled in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person skilled in the art in understanding the described subject matter by providing a description that is more or less independent of any specific vendor's piece(s) of hardware.

The use of functional/operational technical descriptions assists the person skilled in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person skilled in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those skilled in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one skilled in the art can readily understand and apply in a manner independent of a specific vendor's hardware implementation.

At least a portion of the devices or processes described herein can be integrated into an information processing system. An information processing system generally includes one or more of a system unit housing, a video display device, memory, such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), or control systems including feedback loops and control motors (e.g., feedback for detecting position or velocity, control motors for moving or adjusting components or quantities). An information processing system can be implemented utilizing suitable commercially available components, such as those typically found in data computing/communication or network computing/communication systems.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes or systems or other technologies described herein can be effected (e.g., hardware, software, firmware, etc., in one or more machines or articles of manufacture), and that the preferred vehicle will vary with the context in which the processes, systems, other technologies, etc., are deployed. For example, if an implementer determines that speed and accuracy are paramount, the implementer may opt for a mainly hardware or firmware vehicle; alternatively, if flexibility is paramount, the implementer may opt for a mainly software implementation that is implemented in one or more machines or articles of manufacture; or, yet again alternatively, the implementer may opt for some combination of hardware, software, firmware, etc., in one or more machines or articles of manufacture. Hence, there are several possible vehicles by which the processes, devices, other technologies, etc., described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. In an embodiment, optical aspects of implementations will typically employ optically-oriented hardware, software, firmware, etc., in one or more machines or articles of manufacture.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality, and any two components capable of being so associated can also be viewed as being "operably coupleable" to each other to achieve the desired functionality. Specific examples of operably coupleable include, but are not limited to, physically mateable, physically interacting components, wirelessly interactable, wirelessly interacting components, logically interacting, logically interactable components, etc.

In an example embodiment, one or more components may be referred to herein as "configured to," "configurable to," "operable/operative to," "adapted/adaptable," "able to," "conformable/conformed to," etc. Such terms (e.g., "configured to") can generally encompass active-state components, or inactive-state components, or standby-state components, unless context requires otherwise.

The foregoing detailed description has set forth various embodiments of the devices or processes via the use of block diagrams, flowcharts, or examples. Insofar as such block diagrams, flowcharts, or examples contain one or more functions or operations, it will be understood by the reader that each function or operation within such block diagrams, flowcharts, or examples can be implemented, individually or collectively, by a wide range of hardware, software, firmware in one or more machines or articles of manufacture, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is Implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software and/or firmware would be well within the skill of one skilled in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It will be appreciated that variations of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A method for automatic stance classification, said method comprising:
  collecting a plurality of propositions relevant to a query wherein each proposition among said plurality of propositions comprises labeled data;

subjecting said labeled data to a seed word set operation and a non-seed word set operation;

generating a seed lexicon after processing of said seed word set operation; and classifying a stance of each proposition among said plurality of propositions using said seed lexicon and based on whether said each proposition including said labeled data supports said query, opposes said query or is neutral with respect to said query in order to thereafter provide substantive data for decision making based on and extracted from said query; and wherein said stance comprises a medical stance based on word level stance vectors comprising vector representations of a stance context of text and said query comprises a medical query and wherein said word level stance vectors are generated via unsupervised emotion detection that includes a use of a fraction of annotated labeled data and stance vectors created for a seed set of NAVA (Noun, Adjective, Verb, and Adverb) words that form a seed lexicon.

2. The method of claim 1 wherein said stance is classified with a SVM (Support Vector Machine).

3. The method of claim 1 wherein said stance is classified based on an SVM-SC (SVM Based Stance Classification) approach.

4. The method of claim 1 wherein said stance is classified with a classifier comprising a neural network.

5. The method of claim 1 wherein said stance is classified based on an NN-SC (Neural Network Stance Classification) approach comprising a three layer neural network operable to predict a stance category.

6. The method of claim 5 wherein said stance is classified based on an SVM-SC (SVM Based Stance Classification) approach and on said NN-SC approach comprising said three layer neural network.

7. The method of claim 6 further comprising extracting a textual entailment between said query and said at least one proposition and inputting said textual entailment to a classifier for said classifying said stance.

8. The method of claim 1 further comprising extracting a textual entailment between said query and said at least one proposition and inputting said textual entailment to a classifier for said classifying said stance.

9. The method of claim 8 wherein said stance vectors for seed words are constructed by measuring an alignment of each NAVA seed word among said seed set of NAVA words towards three stance categories of: support, oppose, and neutral.

10. The method of claim 1 wherein said stance is attributable to a sentence that is in turn attributable to NAVA words in said sentence.

11. An apparatus for automatic stance classification, said apparatus comprising:

a classifier for classifying a stance of each proposition among a plurality of propositions relevant to a query and using a seed lexicon wherein each proposition among said plurality of propositions comprises labeled data, based on whether said each proposition supports said query, opposes said query, or is neutral with respect to said query in order to thereafter provide substantive data for decision making based on and extracted from said query;

wherein said labeled data is subject to a seed word set operation and a non-seed word set operation and said seed lexicon is generated after processing of said seed word set operation; and wherein said stance comprises a medical stance based on word level stance vectors comprising vector representations of a stance context of text and said query comprises a medical query and wherein said word level stance vectors are generated via unsupervised emotion detection that includes a use of a fraction of annotated labeled data and stance vectors created for a seed set of NAVA (Noun, Adjective, Verb, and Adverb) words that form a seed lexicon.

12. The apparatus of claim 11 wherein said stance is classified by said classifier with a SVM (Support Vector Machine).

13. The apparatus of claim 11 wherein said stance is classified by said classifier based on an SVM-SC (SVM Based Stance Classification) approach.

14. The apparatus of claim 11 wherein said stance is classified by said classifier with a classifier comprising a neural network.

15. The apparatus of claim 11 wherein said stance is classified by said classifier based on an NN-SC (Neural Network Stance Classification Approach) comprising a three layer neural network.

16. The apparatus of claim 11 wherein a textual entailment is extracted between said query and said at least one proposition and inputting said textual entailment to a classifier for said classifying said stance.

17. The apparatus of claim 11 wherein said stance is attributable to a sentence that is in turn attributable to NAVA words in said sentence.

18. A system for automatic stance classification, said system comprising:

at least one processor; and a non-transitory computer-usable medium embodying computer program code, said computer-usable medium capable of communicating with said at least one processor, said computer program code comprising instructions executable by said at least one processor and configured for:

collecting a plurality of propositions relevant to a query wherein each proposition among said plurality of propositions comprises labeled data;

subjecting said labeled data to a seed word set operation and a non-seed word set operation;

generating a seed lexicon after processing of said seed word set operation; and classifying a stance of each proposition among said plurality of propositions using said seed lexicon and based on whether said each proposition including said labeled data supports said query, opposes said query or is neutral with respect to said query in order to thereafter provide substantive data for decision making based on and extracted from said query; and creating annotated labeled data and stance vectors for a seed set of NAVA (Noun, Adjective, Verb, and Adverb) words that form a seed lexicon, wherein said stance comprises a medical stance based on word level stance vectors comprising vector representations of a stance context of text and said query comprises a medical query and wherein said word level stance vectors are generated via unsupervised emotion detection that includes a use of a fraction of the annotated labeled data and the stance vectors created for the seed set of the NAVA (Noun, Adjective, Verb, and Adverb) words that form the seed lexicon.

19. The system of claim 18 wherein said stance is classified with a SVM (Support Vector Machine).

20. The system of claim 18 wherein said stance is classified with a classifier comprising a neural network.

* * * * *